United States Patent
Axelson, Jr. et al.

(10) Patent No.: US 11,406,506 B2
(45) Date of Patent: Aug. 9, 2022

(54) GLENOID IMPLANT SYSTEMS AND METHODS OF USING THE SAME

(71) Applicant: Encore Medical, L.P., Austin, TX (US)

(72) Inventors: Stuart L. Axelson, Jr., Succasunna, NJ (US); Christina Marie Risley, West Barnstable, MA (US); Samantha Jorge Rogers, Somerset, MA (US); Frank Joseph Arturi, West Harrison, NY (US); Erik Richard Kareliussen, Clinton, CT (US); Austin Marek Salkind, Rochester, MA (US)

(73) Assignee: Encore Medical, L.P., Austin, TX (US)

( * ) Notice: Subject to any disclaimer, the term of this patent is extended or adjusted under 35 U.S.C. 154(b) by 0 days.

(21) Appl. No.: 17/594,571

(22) PCT Filed: Apr. 24, 2020

(86) PCT No.: PCT/US2020/029932
§ 371 (c)(1),
(2) Date: Oct. 22, 2021

(87) PCT Pub. No.: WO2020/219962
PCT Pub. Date: Oct. 29, 2020

(65) Prior Publication Data
US 2022/0142789 A1    May 12, 2022

Related U.S. Application Data

(60) Provisional application No. 62/838,792, filed on Apr. 25, 2019.

(51) Int. Cl.
*A61F 2/40*    (2006.01)
*A61F 2/30*    (2006.01)

(52) U.S. Cl.
CPC ...... *A61F 2/4081* (2013.01); *A61F 2002/305* (2013.01); *A61F 2002/30113* (2013.01);
(Continued)

(58) Field of Classification Search
CPC ............ A61F 2/4081; A61F 2002/3437; A61F 2002/4022; A61F 2002/4037; A61F 2002/4085
See application file for complete search history.

(56) References Cited

U.S. PATENT DOCUMENTS

| | | |
|---|---|---|
| 4,550,450 A | 11/1985 | Kinnett |
| 4,964,865 A | 10/1990 | Burkhead et al. |

(Continued)

OTHER PUBLICATIONS

International Search Report and Written Opinion of International Searching Authority for Application No. PCT/US2020/029932, dated Jul. 27, 2020 (8 pages).

*Primary Examiner* — Megan Y Wolf
(74) *Attorney, Agent, or Firm* — Nixon Peabody LLLP

(57) ABSTRACT

A glenoid implant system includes an anchoring structure and a glenoid liner. The anchoring structure includes a base, a wall, and a ledge. The wall extends from a first surface of the base. The ledge extends generally along at least a portion of a first side of the wall, thereby forming an undercut. The wall has a slot formed in a second opposing side of the wall. The glenoid liner is configured to be removably coupled to the anchoring structure. The glenoid liner has a cap portion, a main body, and a deflectable finger. The main body extends from the cap portion and includes a lip configured to engage the undercut of the anchoring structure. The deflectable finger extends from the cap portion. The deflectable finger has a protrusion configured to engage the slot of the anchoring structure to aid in securing the glenoid liner to the anchoring structure.

19 Claims, 11 Drawing Sheets

(52) U.S. Cl.
CPC ............ *A61F 2002/30125* (2013.01); *A61F 2002/30133* (2013.01); *A61F 2002/30604* (2013.01); *A61F 2002/30892* (2013.01); *A61F 2002/4085* (2013.01)

(56) References Cited

U.S. PATENT DOCUMENTS

| | | | |
|---|---|---|---|
| 6,679,916 B1 | 1/2004 | Frankle et al. | |
| 8,070,820 B2 | 12/2011 | Winslow et al. | |
| 9,283,075 B2 | 3/2016 | Wiley et al. | |
| 2001/0011192 A1 | 8/2001 | Ondrla et al. | |
| 2006/0200248 A1 | 9/2006 | Beguin et al. | |
| 2014/0236304 A1* | 8/2014 | Hodorek | A61F 2/4637 623/19.14 |
| 2014/0324179 A1* | 10/2014 | Salehi | A61F 2/389 623/20.32 |
| 2017/0056187 A1 | 3/2017 | Humphrey et al. | |
| 2021/0307918 A1* | 10/2021 | Deransart | A61F 2/4003 |

* cited by examiner

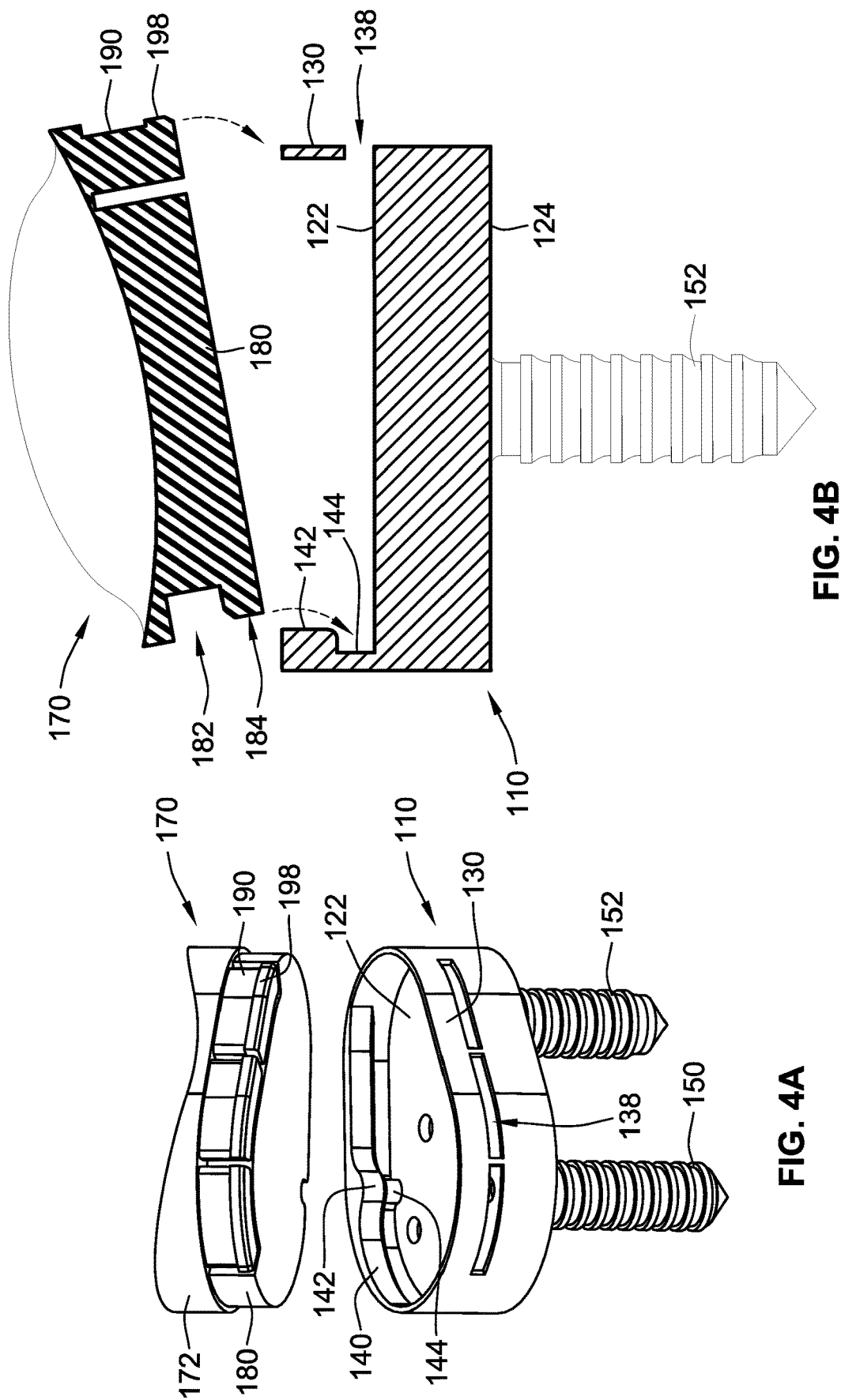

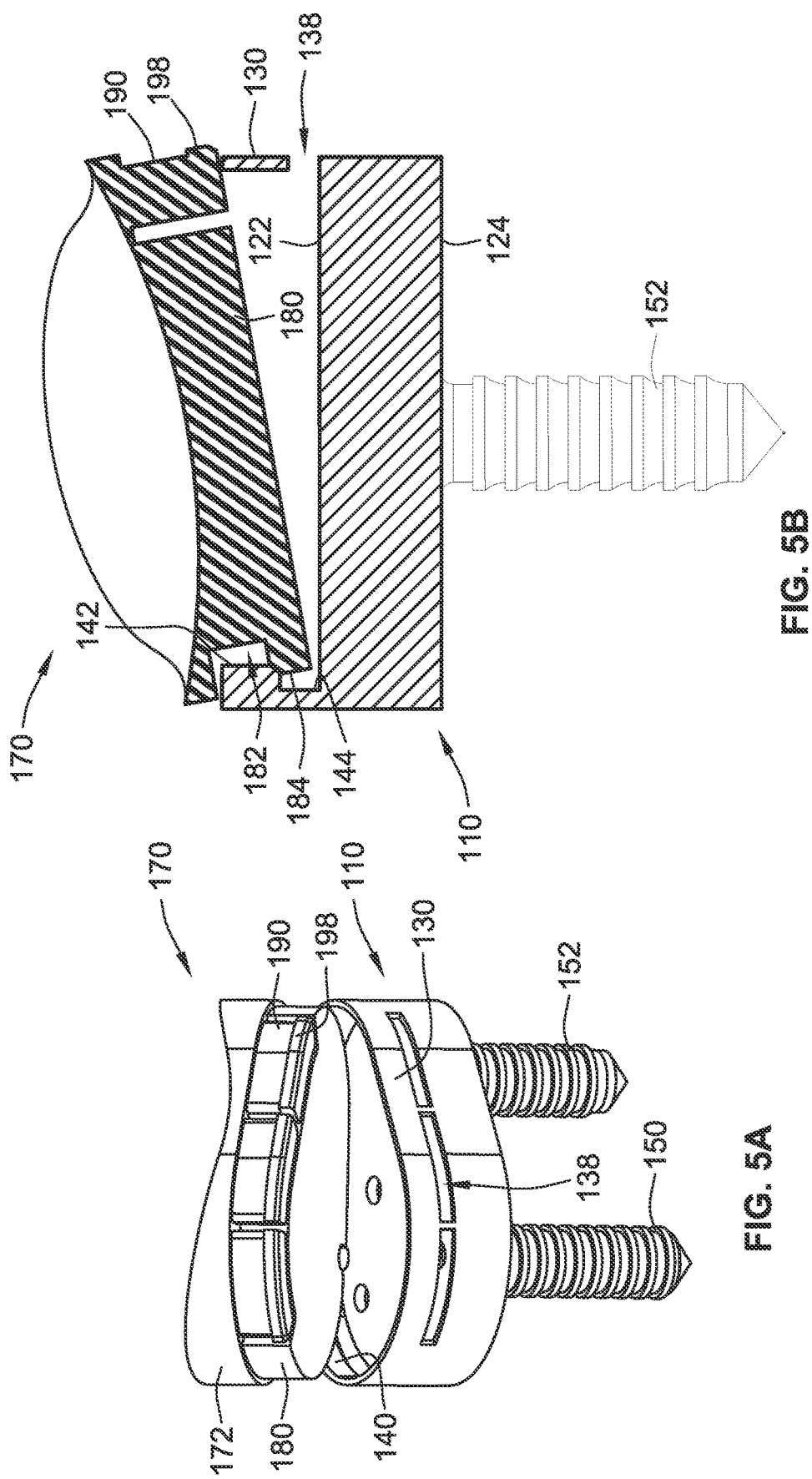

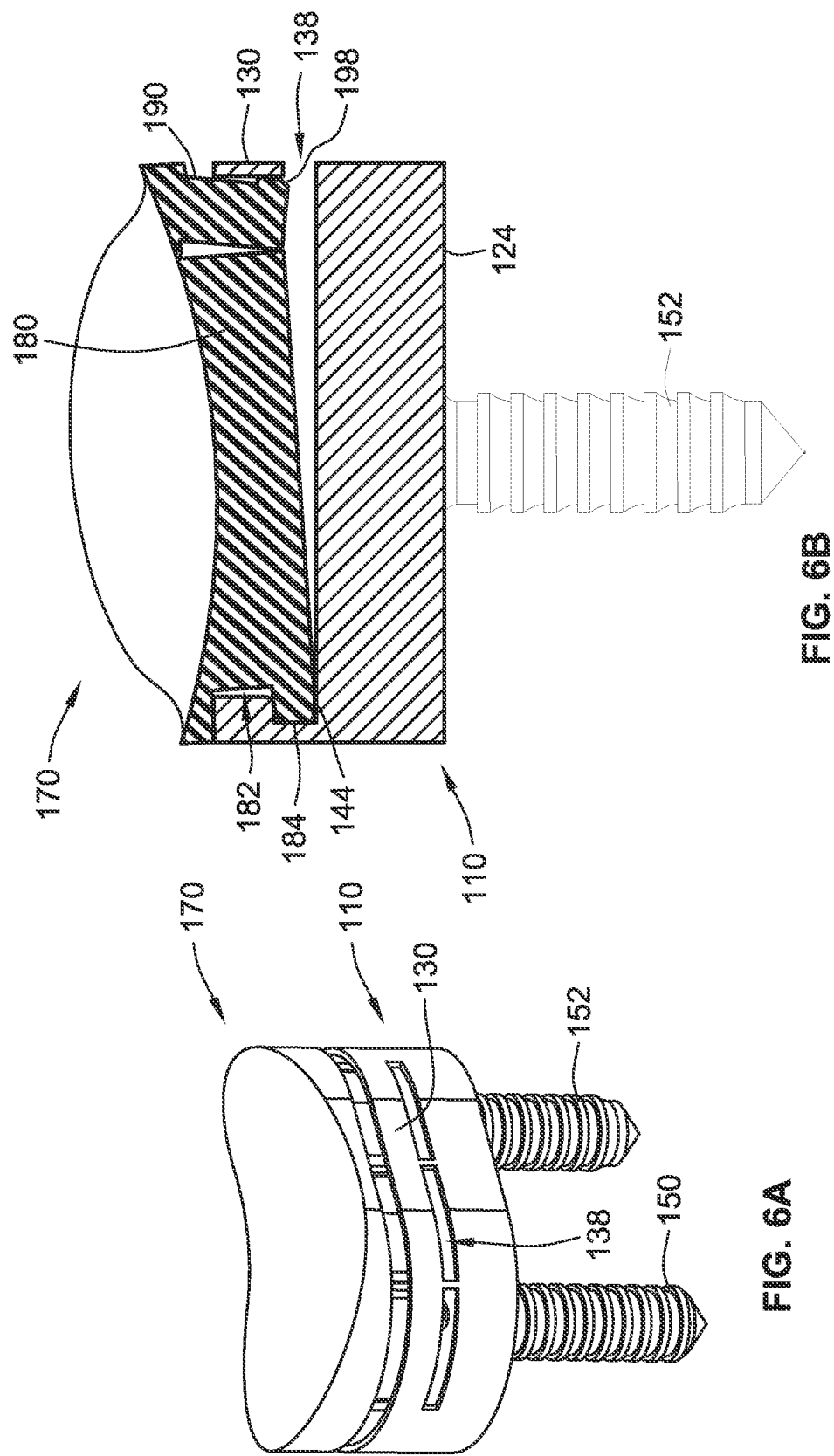

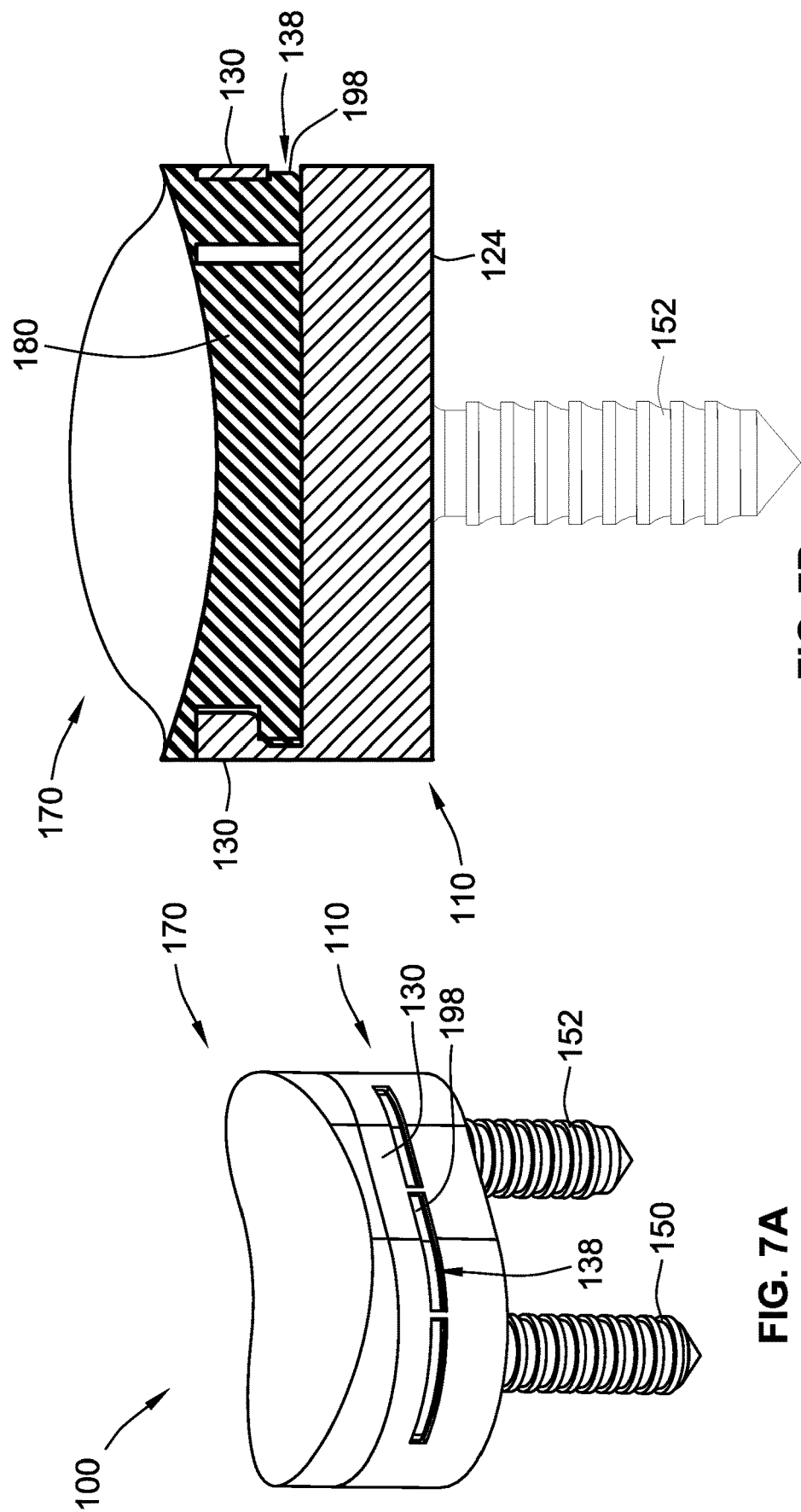

GLENOID IMPLANT SYSTEMS AND METHODS OF USING THE SAME

CROSS-REFERENCE TO RELATED APPLICATIONS

This application is the National Phase of International Application PCT/US2020/029932, filed Apr. 24, 2020, which designated the United States, which claims priority to and the benefit of U.S. Provisional Patent Application No. 62/838,792, filed on Apr. 25, 2019, each of which is hereby incorporated by reference herein in its entirety.

TECHNICAL FIELD

This disclosure relates generally to shoulder implants, and more particularly, to glenoid implants.

BACKGROUND

Shoulder arthroplasty is used to treat acute osteoarthritis or a shoulder joint fracture. There are two common forms of shoulder arthroplasty: total shoulder arthroplasty (TSA) and reverse shoulder arthroplasty (RSA). TSA uses a metal ball component at the humeral head, which mates into a polyethylene cup on the glenoid. RSA switches the locations between the head and the cup, such that the humerus becomes the cup and the glenoid becomes the head. RSA can be performed as a revision to TSA, allowing greater functionality for patients with rotator cuff tears. RSA utilizes the patient's deltoid to control the movements of the shoulder.

Thus, a need exists for a shoulder implant that is bone conserving and also versatile for revision. The present disclosure is directed to solving these problems and addressing other needs.

SUMMARY

According to some implementations of the present disclosure, a glenoid implant system includes an anchoring structure and a glenoid liner. The anchoring structure includes a base, a wall, and a ledge. The wall extends from a first surface of the base. The ledge extends generally along at least a portion of a first side of the wall, thereby forming an undercut. The wall has a slot formed in a second opposing side of the wall. The glenoid liner is configured to be removably coupled to the anchoring structure. The glenoid liner has a cap portion, a main body, and a deflectable finger. The cap portion has a first surface and a second opposing surface. The main body extends from the second opposing surface of the cap portion and includes a lip configured to engage the undercut of the anchoring structure. The deflectable finger extends from the second opposing surface of the cap portion. The deflectable finger has a protrusion configured to engage the slot of the anchoring structure to aid in securing the glenoid liner to the anchoring structure.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 4A illustrates a first step of assembling the glenoid implant system of FIG. 1, according to some implementations of the present disclosure;

FIG. 4B illustrates a cross-sectional view of the first step of assembling the glenoid implant system of FIG. 1, according to some implementations of the present disclosure;

FIG. 5A illustrates a second step of assembling the glenoid implant system of FIG. 1, according to some implementations of the present disclosure;

FIG. 5B illustrates a cross-sectional view of the second step of assembling the glenoid implant system of FIG. 5A, according to some implementations of the present disclosure;

FIG. 6A illustrates a third step of assembling the glenoid implant system of FIG. 1, according to some implementations of the present disclosure;

FIG. 6B illustrates a cross-sectional view of the third step of assembling the glenoid implant system of FIG. 6A, according to some implementations of the present disclosure;

FIG. 7A illustrates an assembled glenoid implant system of FIG. 1, according to some implementations of the present disclosure;

FIG. 7B illustrates a cross-sectional view of the assembled glenoid implant system of FIG. 7A, according to some implementations of the present disclosure;

Figure 1:
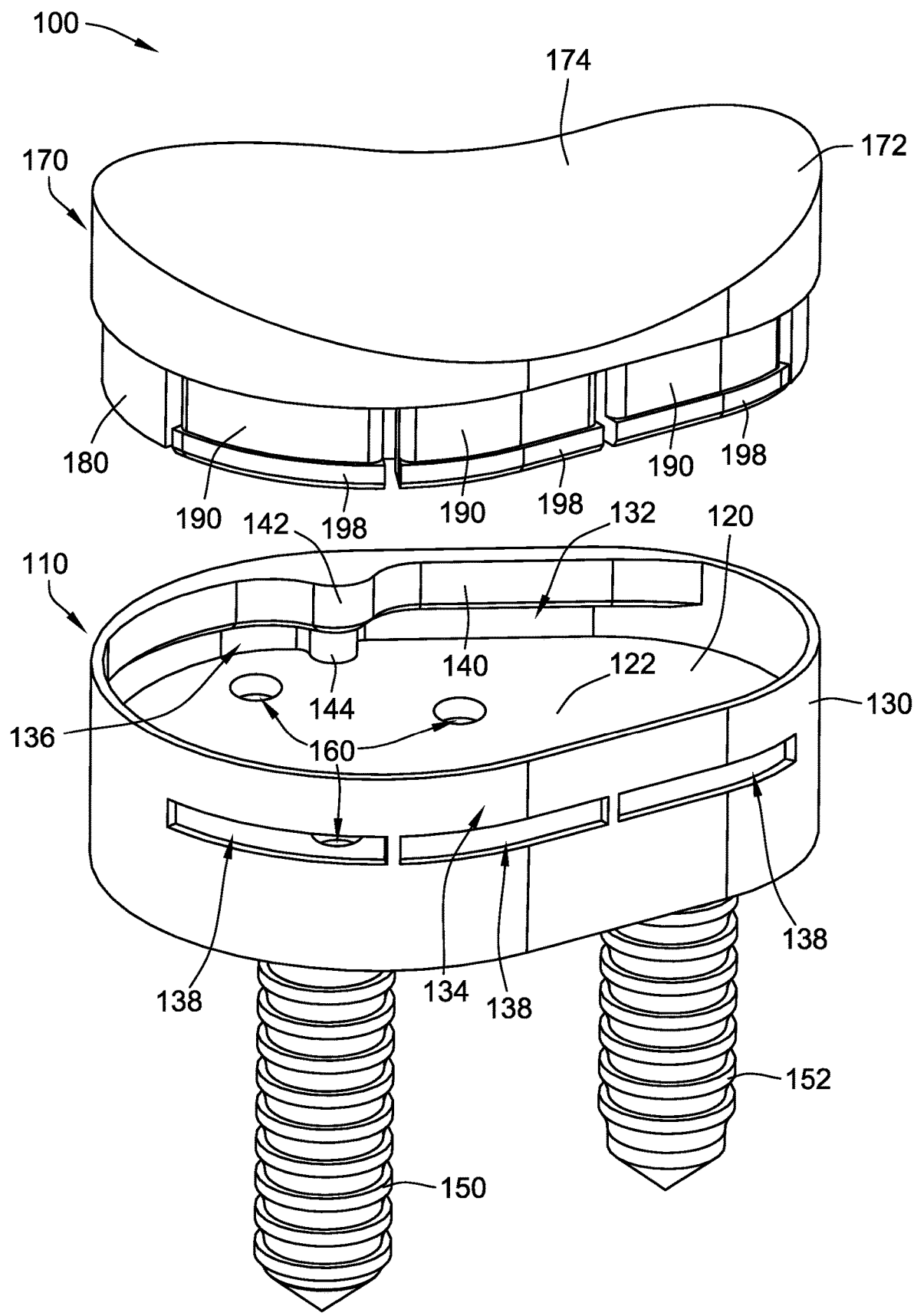
FIG. 1 illustrates a first disassembled perspective view of a glenoid implant system, according to some implementations of the present disclosure.

While the present disclosure is susceptible to various modifications and alternative forms, specific implementations have been shown by way of example in the drawings and will be described in further detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration.

Figure 2:
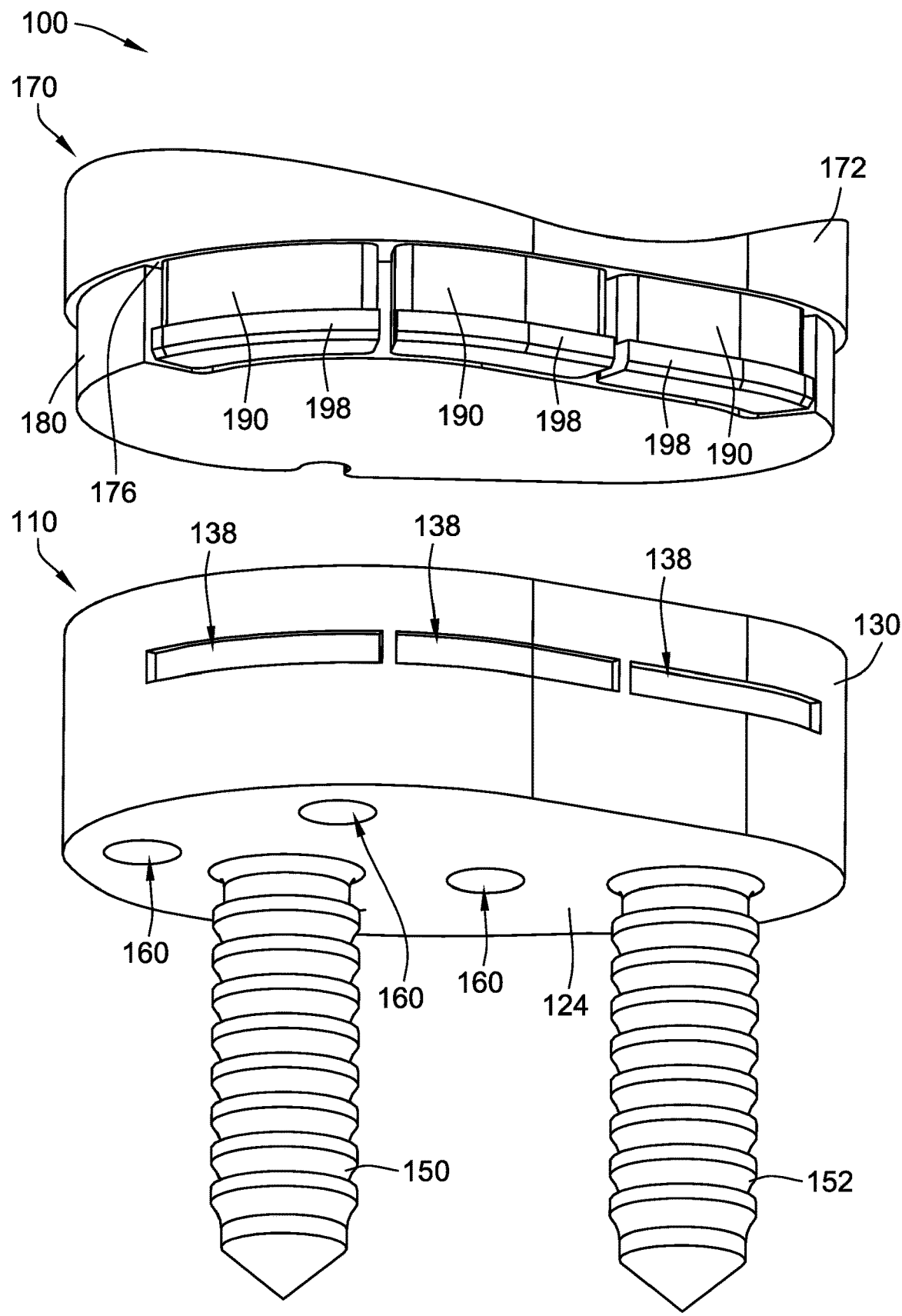
FIG. 2 illustrates a second disassembled perspective view of the glenoid implant system of FIG. 1, according to some implementations of the present disclosure.

Referring generally to FIGS. 1-2, a disassembled view of a glenoid implant system 100 is illustrated, according to some implementations of the present disclosure. The glenoid implant system 100 includes an anchoring structure 110 and a glenoid liner 170 (e.g., an anatomic glenoid liner).

The anchoring structure 110 includes a base 120, a wall 130, and a ledge 140. The wall 130 extends from a first surface 122 of the base 120. For example, in some implementations, the wall 130 of the anchoring structure 110 extends generally perpendicularly from the first surface 122 of the base 120. The ledge 140 of the anchoring structure 110 extends from an inside surface of the wall 130 as opposed to an outside surface of the wall 130. Further, the ledge 140 extends generally along at least a portion of a first side 132 of the wall 130, thereby forming an undercut 136. In some implementations, the transition from the ledge 140 to the undercut 136 includes a straight edge, a bevel, a chamfer, or any combination thereof. The wall 130 includes a slot 138 formed in a second opposing side 134 of the wall 130. Additionally, in some implementations, the anchoring structure 110 can include a porous coating, for example, around the wall 130 of the anchoring structure 110. The porous coating can aid in osseointegration with the bone of a patient having the glenoid implant system installed and/or implanted.

The glenoid liner 170 includes a cap portion 172, a main body 180, and a plurality of deflectable fingers 190. The main body 180 extends from the second opposing surface of the cap portion 172. Each deflectable finger 190 also extends from the second opposing surface 176 of the cap portion 172. In some implementations, the glenoid liner 170 is one monolithic part. In some other implementations, one or more components of the glenoid liner 170 is separate and distinct from the remaining components of the glenoid liner 170. The cap portion 172 includes a first surface 174, and a second opposing surface 176. In some implementations, the first surface 174 of the cap portion 172 is generally concave. For example, in some implementations, the first surface 174 of the cap portion 172 is rounded and may resemble the shape of a healthy human glenoid bone. In some implementations, the second opposing surface 176 of the cap portion 172 is generally planar.

The glenoid liner 170 is configured to be removably coupled to the anchoring structure 110. There are several components that aid in securing the glenoid liner 170 to the anchoring structure 110. First, in some implementations, the main body 180 includes a lip 186 configured to engage the undercut 136 of the anchoring structure 110.

Second, in some implementations, each deflectable finger 190 includes a protrusion 198, which is configured to engage the slot 138 of the anchoring structure 110 to aid in securing the glenoid liner 170 to the anchoring structure 110. For example, in some implementations, the protrusion 198 of the deflectable finger 190 includes an elongated rib, a ball, a hook, or any combination thereof. Further, in some implementations, each deflectable finger 190 is snap-locked into the corresponding slot 138 of the anchoring structure 110 via the protrusion 198. Additionally, or alternatively, in some implementations, the glenoid liner 170 includes a plurality of snap fasteners that are configured to engage one or more of the slots 138 of the anchoring structure 110 to aid in securing the glenoid liner 170 to the anchoring structure 110.

Figure 3:
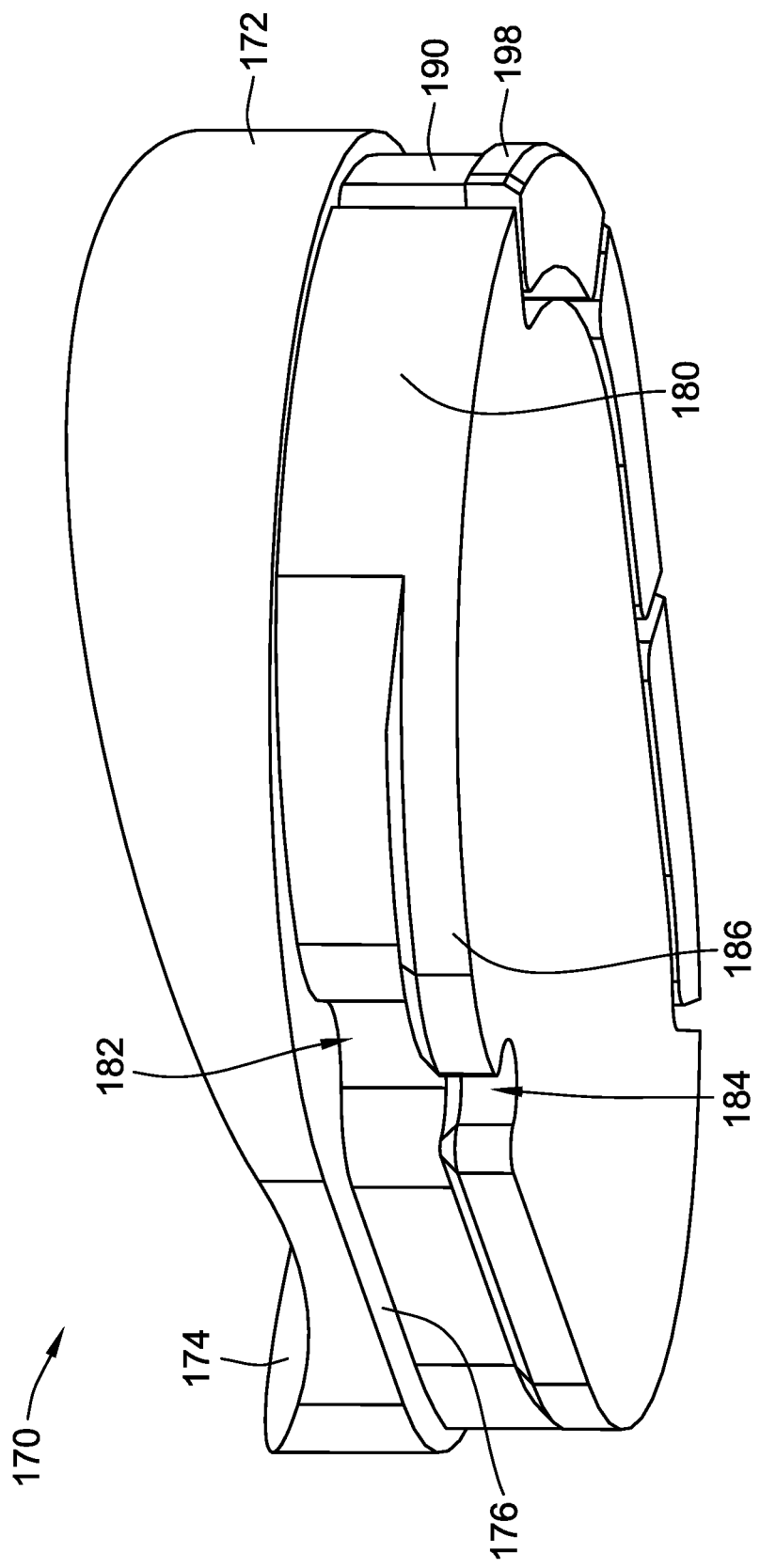
FIG. 3 illustrates a perspective view of a glenoid liner of the glenoid implant system of FIG. 1, according to some implementations of the present disclosure.

Third, in some implementations, the ledge 140 of the anchoring structure 110 includes a first protrusion 142. The first protrusion 142 is configured to engage a first corresponding notch 182 formed in the main body 180 of the glenoid liner 170. As best shown in FIG. 3, the first corresponding notch 182 is positioned generally between the cap portion 172 of the glenoid liner 170 and the lip 186 of the main body 180 of the glenoid liner 170.

Fourth, in some implementations, the anchoring structure 110 further includes a second protrusion 144, which is positioned generally between the first protrusion 142 of the ledge 140 and the base 120 of the anchoring structure 110. The second protrusion 144 is configured to engage a second corresponding notch 184 formed in the lip 186 of the main body 180 of the glenoid liner 170 (as best shown in FIG. 3).

In some implementations, the first protrusion 142 extends a first distance from the wall 130. The second protrusion 144 extends a second distance from the wall 130 that is less than the first distance. Additionally, or alternatively, in some implementations, the first protrusion 142 is stacked on the second protrusion 144 in a stepped fashion.

While the glenoid implant system 100 is shown in FIGS. 1-7B as including at least four sets of components that aid in securing the glenoid liner 170 to the anchoring structure 110 (e.g., the lip 186 of the main body 180 configured to engage the undercut 136 of the anchoring structure 110; the protrusion 198 of each deflectable finger 190 configured to engage the corresponding slot 138 of the anchoring structure 110; the first protrusion 142 of the ledge 140 of the anchoring structure 110 configured to engage the first corresponding notch 182 formed in the main body 180 of the glenoid liner 170; and the second protrusion 144 of the anchoring structure 110 configured to engage the second corresponding notch 184 formed in the lip 186 of the main body 180 of the glenoid liner 170), a glenoid implant system of the present disclosure can include more or fewer sets of components that aid in securing the glenoid liner 170 to the anchoring structure 110.

As an example, in some implementations, a first alternative glenoid implant system can include the lip 186 of the main body 180 configured to engage the undercut 136 of the anchoring structure 110; and the protrusion 198 of each deflectable finger 190 configured to engage the corresponding slot 138 of the anchoring structure 110.

As another example, in some implementations, a second alternative glenoid implant system can include the protrusion 198 of each deflectable finger 190 configured to engage the corresponding slot 138 of the anchoring structure 110; the first protrusion 142 of the ledge 140 of the anchoring structure 110 configured to engage the first corresponding notch 182 formed in the main body 180 of the glenoid liner 170; and the second protrusion 144 of the anchoring structure 110 configured to engage the second corresponding notch 184 formed in the lip 186 of the main body 180 of the glenoid liner 170.

As a further example, in some implementations, a third alternative glenoid implant system can include the lip 186 of the main body 180 configured to engage the undercut 136 of the anchoring structure 110; the protrusion 198 of each deflectable finger 190 configured to engage the corresponding slot 138 of the anchoring structure 110; and the second protrusion 144 of the anchoring structure 110 configured to engage the second corresponding notch 184 formed in the lip 186 of the main body 180 of the glenoid liner 170.

As yet another example, in some implementations, a fourth alternative glenoid implant system can include the lip 186 of the main body 180 configured to engage the undercut 136 of the anchoring structure 110; the protrusion 198 of each deflectable finger 190 configured to engage the corresponding slot 138 of the anchoring structure 110; and the first protrusion 142 of the ledge 140 of the anchoring structure 110 configured to engage the first corresponding notch 182 formed in the main body 180 of the glenoid liner 170.

As an additional example, in some implementations, a fifth alternative glenoid implant system can include a dovetail locking mechanism on the first side 132 of the wall 130 that is configured to engage a mating dovetail locking mechanism on the main body 180; and the protrusion 198 of each deflectable finger 190 configured to engage the corresponding slot 138 of the anchoring structure 110.

While it is shown in FIG. 1 that the base 120 of the anchoring structure 110 is generally egg shaped, the base 120 of the anchoring structure 110 can have any suitable shapes. For example, in some implementations, the base 120 of the anchoring structure 110 is generally circular, generally oval, generally bean shaped, generally egg shaped, generally tear-drop shaped, generally football shaped, or any combination thereof.

Still referring to FIGS. 1-2, the anchoring structure 110 is configured to be anchored in a glenoid cavity of a patient. In some implementations, the anchoring structure 110 further includes a first anchoring peg 150 extending from a second opposing surface 124 of the base 120 opposite the first surface 122 of the base 120 (e.g., across the base 120). In some such implementations, the anchoring structure 110 can further include a second anchoring peg 152 extending from the second opposing surface 124 of the base 120, where the second anchoring peg 152 is spaced from the first anchoring peg 150. While in some implementations, only one anchoring peg is needed, having both the first anchoring peg 150 and the second anchoring peg 152 is advantageous to prevent any unwanted rotation of the anchoring structure 110 once it is installed into the patient.

In some implementations, the first anchoring peg 150 and the second anchoring peg 152 are the same, and have ridges that flex when press fit into the bone (e.g., the glenoid cavity) of the patient. In some implementations, the ridges aid in the osseointegration of the anchoring peg 150 to the bone of the patient. Alternatively, in some implementations, in place of the first anchoring peg 150, the anchoring structure 110 includes a first screw hole for a center screw to attach the anchoring structure 110 to the bone (e.g., the glenoid cavity) of the patient. Additionally, or alternatively, in some implementations, in place of the second anchoring peg 152, the anchoring structure 110 includes a second screw hole for a side screw to attach the anchoring structure 110 to the bone (e.g., the glenoid cavity) of the patient.

Furthermore, in some implementations, to aid in securing the anchoring structure 110 to a glenoid fossa of a patient, the base 120 of the anchoring structure 110 further includes a plurality of through-holes 160 for receiving one or more respective fasteners therethrough. The plurality of through-holes 160 can be straight, angled, or both.

In some implementations, the second opposing surface 124 of the base 120 is generally planar for coupling to a corresponding generally planar surface of the glenoid fossa of the patient. For example, in some implementations, the generally planar second opposing surface 124 of the base 120 can be more bone-conserving, which sits on the reamed surface of the glenoid focca. In some other implementations, the second opposing surface 124 of the base 120 is generally convex for coupling to a corresponding generally concave surface of the glenoid fossa of the patient.

As disclosed herein, the glenoid liner 170 is configured to be removably coupled to the anchoring structure 110. Some examples of the steps for coupling the glenoid liner 170 to the anchoring structure 110 are illustrated in FIGS. 4A-7B, according to some implementations of the present disclosure.

Referring to FIGS. 4A-4B, a first step of assembling the glenoid implant system 100 is illustrated in its perspective view (FIG. 4A) and its cross-sectional view (FIG. 4B), according to some implementations of the present disclosure. The same reference numbers in FIGS. 4A-4B are used for the same elements in FIGS. 1-3. The glenoid liner 170 is angled and/or tilted such that the lip 186 of the glenoid liner 170 is closer to the first side 132 (FIG. 1) of the wall 130, than the plurality of deflectable fingers 190 is to the second opposing side 132 (FIG. 1) of the wall 130. In addition, in some implementations, the first corresponding notch 182 formed in the main body 180 of the glenoid liner 170 is being aligned vertically with the first protrusion 142 of the ledge 140 of the anchoring structure 110. Additionally, or alternatively, in some implementations, the second corresponding notch 184 formed in the lip 186 of the main body 180 of the glenoid liner 170 is being aligned vertically with the second protrusion 144 of the anchoring structure 110.

Referring to FIGS. 5A-5B, a second step of assembling the glenoid implant system 100 is illustrated in its perspective view (FIG. 5A) and its cross-sectional view (FIG. 5B), according to some implementations of the present disclosure. The same reference numbers in FIGS. 5A-5B are used for the same elements in FIGS. 1-3. The lip 186 of the main body 180 is inserted to engage the undercut 136 of the anchoring structure 110. In addition, in some implementations, the first protrusion 142 of the ledge 140 of the anchoring structure 110 is inserted to engage the first corresponding notch 182 formed in the main body 180 of the glenoid liner 170. Additionally, or alternatively, in some implementations, the second protrusion 144 of the anchoring structure 110 is inserted to engage the second corresponding notch 184 formed in the lip 186 of the main body 180 of the glenoid liner 170.

Further, in some implementations, the plurality of deflectable fingers 190 of the glenoid liner 170 is pushed inward and downward relative to the wall 130 of the anchoring structure 110, so that the protrusion 198 of each deflectable finger 190 can move past a portion of the wall 130 that is above the corresponding slot 138.

Referring to FIGS. 6A-6B, a third step of assembling the glenoid implant system 100 is illustrated in its perspective view (FIG. 6A) and its cross-sectional view (FIG. 6B), according to some implementations of the present disclosure. The same reference numbers in FIGS. 6A-6B are used for the same elements in FIGS. 1-3. The lip 186 of the main body 180 is almost fully engaged with the undercut 136 of the anchoring structure 110. In addition, in some implementations, the first protrusion 142 of the ledge 140 of the anchoring structure 110 is almost fully engaged with the first corresponding notch 182 formed in the main body 180 of the glenoid liner 170. Additionally, or alternatively, in some implementations, the second protrusion 144 of the anchoring structure 110 is almost fully engaged with the second corresponding notch 184 formed in the lip 186 of the main body 180 of the glenoid liner 170.

Further, the protrusion 198 of each deflectable finger 190 has almost moved past the portion of the wall 130 that is above the corresponding slot 138. In some implementations, the plurality of deflectable fingers 190 of the glenoid liner 170 is further pushed downward (e.g., toward the base 120 of the anchoring structure 110), so that the plurality of deflectable fingers 190 can spring back (e.g., deflect back to its original position) to allow the protrusion 198 of each deflectable finger 190 to engage the corresponding slot 138 of the anchoring structure 110.

Referring to FIGS. 7A-7B, an assembled glenoid implant system 100 is illustrated in its perspective view (FIG. 7A) and its cross-sectional view (FIG. 7B), according to some implementations of the present disclosure. The same reference numbers in FIGS. 7A-7B are used for the same elements in FIGS. 1-3. The lip 186 of the main body 180 is engaged with the undercut 136 of the anchoring structure 110. In addition, the first protrusion 142 of the ledge 140 of the anchoring structure 110 is engaged with the first corresponding notch 182 formed in the main body 180 of the glenoid liner 170. The second protrusion 144 of the anchoring structure 110 is also engaged with the second corresponding notch 184 formed in the lip 186 of the main body 180ff of the glenoid liner 170.

Further, the plurality of deflectable fingers 190 of the glenoid liner 170 has snapped down and into the corresponding slots 138 of the anchoring structure 110, and the protrusion 198 of each deflectable finger 190 is engaged with the corresponding slot 138 of the anchoring structure 110. In addition, the wall 130 extends about an entire perimeter of the base 120 (as best shown in FIG. 1). As such, when assembled, the main body 180 of the glenoid liner 170 is configured to be encapsulated within the wall 130 of the anchoring structure 110.

Figure 8A:
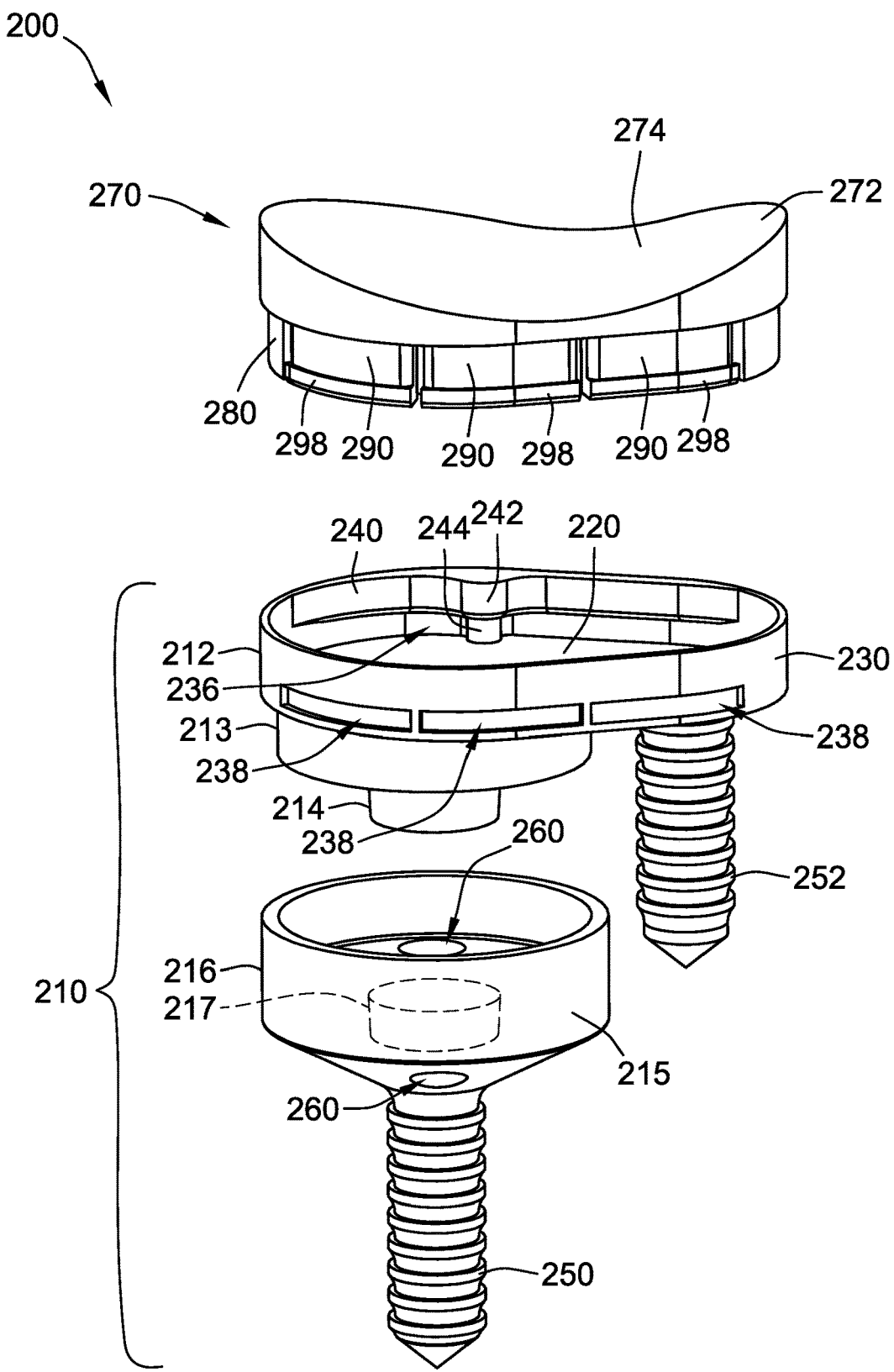
FIG. 8A illustrates a disassembled perspective view of a first alternative glenoid implant system, according to some implementations of the present disclosure.
Figure 8B:
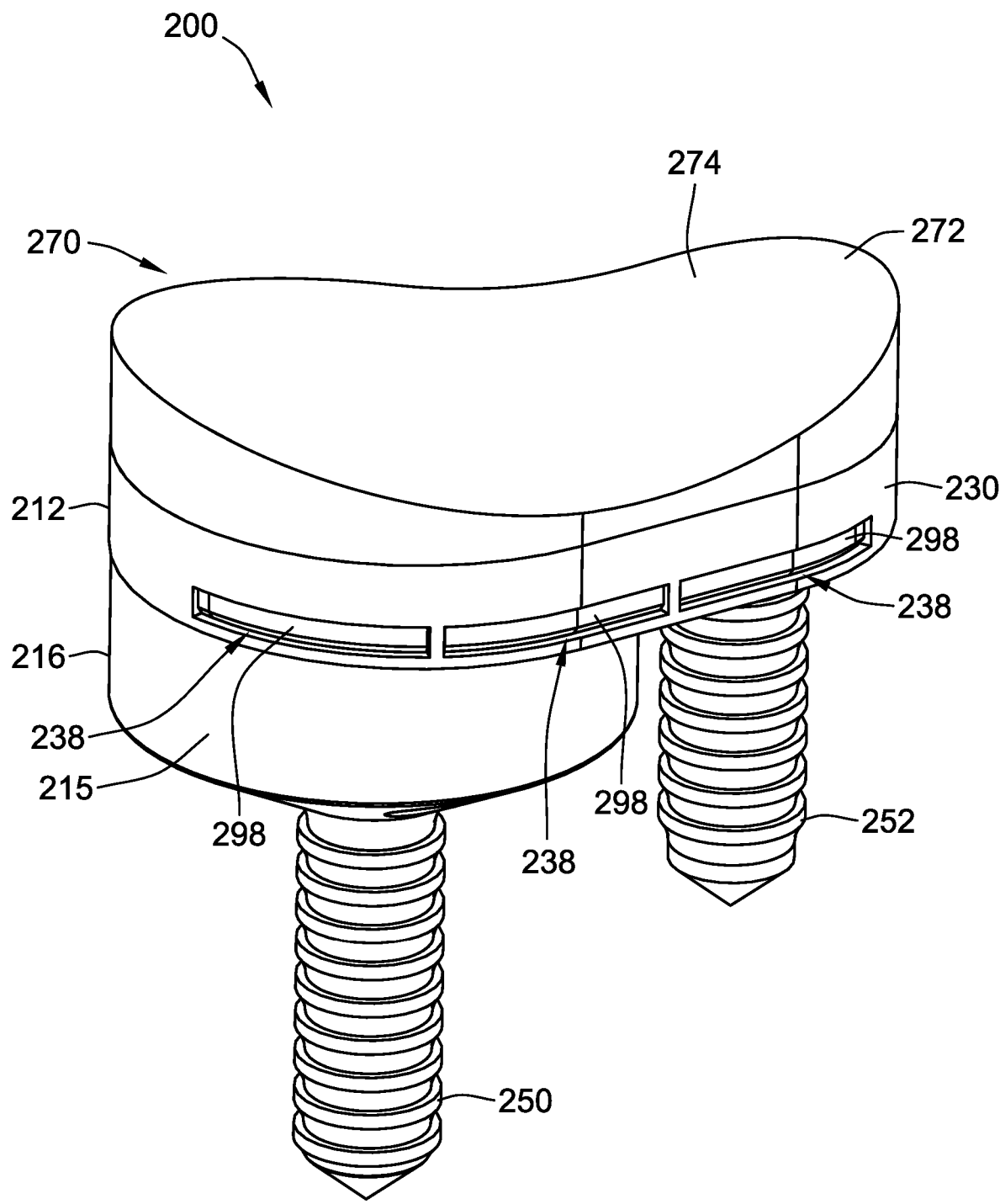
FIG. 8B illustrates an assembled perspective view of the first alternative glenoid implant system of FIG. 8A, according to some implementations of the present disclosure.

Turning now to FIGS. 8A-8B, a first alternative glenoid implant system 200 is illustrated in its disassembled view of (FIG. 8A) and its assembled view (FIG. 8B), according to some implementations of the present disclosure. The glenoid implant system 200 is the same as, or similar to, the glenoid implant system 100, where like reference numbers are used for like elements, except that the anchoring structure 210 of the glenoid implant system 200 includes a baseplate 216 and a glenoid liner adapter 212 (e.g., an anatomic glenoid liner adapter).

In some implementations, the glenoid implant system 200 (including, for example, the baseplate 216, the glenoid liner adapter 212, and the glenoid liner 270) can be used for TSA (e.g., an anatomic procedure). The anatomic procedure can involve the repair and/or replacement of the affected extremity's ball and socket joint after years of degeneration. This surgery involves replacing the ball portion of the shoulder, which is also referred to as the humeral head, with a metal sphere while a plastic or other synthetic apparatus is used for the socket replacement. This type of procedure is most helpful for patients with arthritis and other related conditions, which result in joint problems and missing cartilage.

As shown in FIG. 8A, the glenoid liner 270 of the glenoid implant system 200 is the same as, or similar to, the glenoid liner 170 of the glenoid implant system 100. The glenoid liner 270 is configured to be coupled to the glenoid liner adapter 212, in the same or similar manner as what is disclosed and illustrated with reference to FIGS. 4A-7B.

The glenoid liner adapter 212 is configured to be coupled to the baseplate 216. The glenoid liner adapter 212 includes stacked protuberances 213 and 214 extending from the base 220. The stacked protuberances 213 and 214 are spaced from the second anchoring peg 252. The baseplate 216 includes a wall (e.g., a shell, a peripheral rim) 215 configured to receive the first protuberance 213. In some implementations, the coupling mechanism between the wall 215 and the first protuberance 213 includes an interference fit, a spring fit, a Morse Taper lock, or any combination thereof. Additionally, or alternatively, in some implementations, the baseplate 216 includes a cavity 217 configured to receive the second protuberance 214. The coupling mechanism between the cavity 217 and the second protuberance 214 can include an interference fit, a spring fit, a Morse Taper lock, or any combination thereof. Additionally, or alternatively, in some implementations, the glenoid liner adapter 212 is configured to be coupled to the baseplate 216 via a center screw.

In some implementations, the baseplate 216 includes peripheral screw holes 260 located around the cavity 217. The peripheral screw holes 260 can be used for straight and/or angled screws. Further, in some implementations, the wall 215 of the baseplate 216 provides added stability against edge loading. Additionally, in some implementations, the baseplate 216 can include a porous coating, for example, around the wall 215 of the baseplate 216.

As disclosed herein, TSA uses a metal ball component at the humeral head, which mates into a polyethylene cup on the glenoid. RSA switches the locations between the head and the cup, such that the humerus becomes the cup and the glenoid becomes the head. RSA can be performed as a revision to TSA, allowing greater functionality for patients with rotator cuff tears. RSA utilizes the patient's deltoid to control the movements of the shoulder. The revision from TSA to RSA involves the replacement of both the glenoid component and the humeral component. On the glenoid side, the cemented glenoid component is replaced by a metal baseplate and screws. On the humeral side, the stem and the head are removed and replaced with new RSA components. The conversion shoulder arthroplasty corrects the failure of the TSA due to loosened implants, wear, infection, and/or shoulder dislocation or misalignment.

Figure 9A:
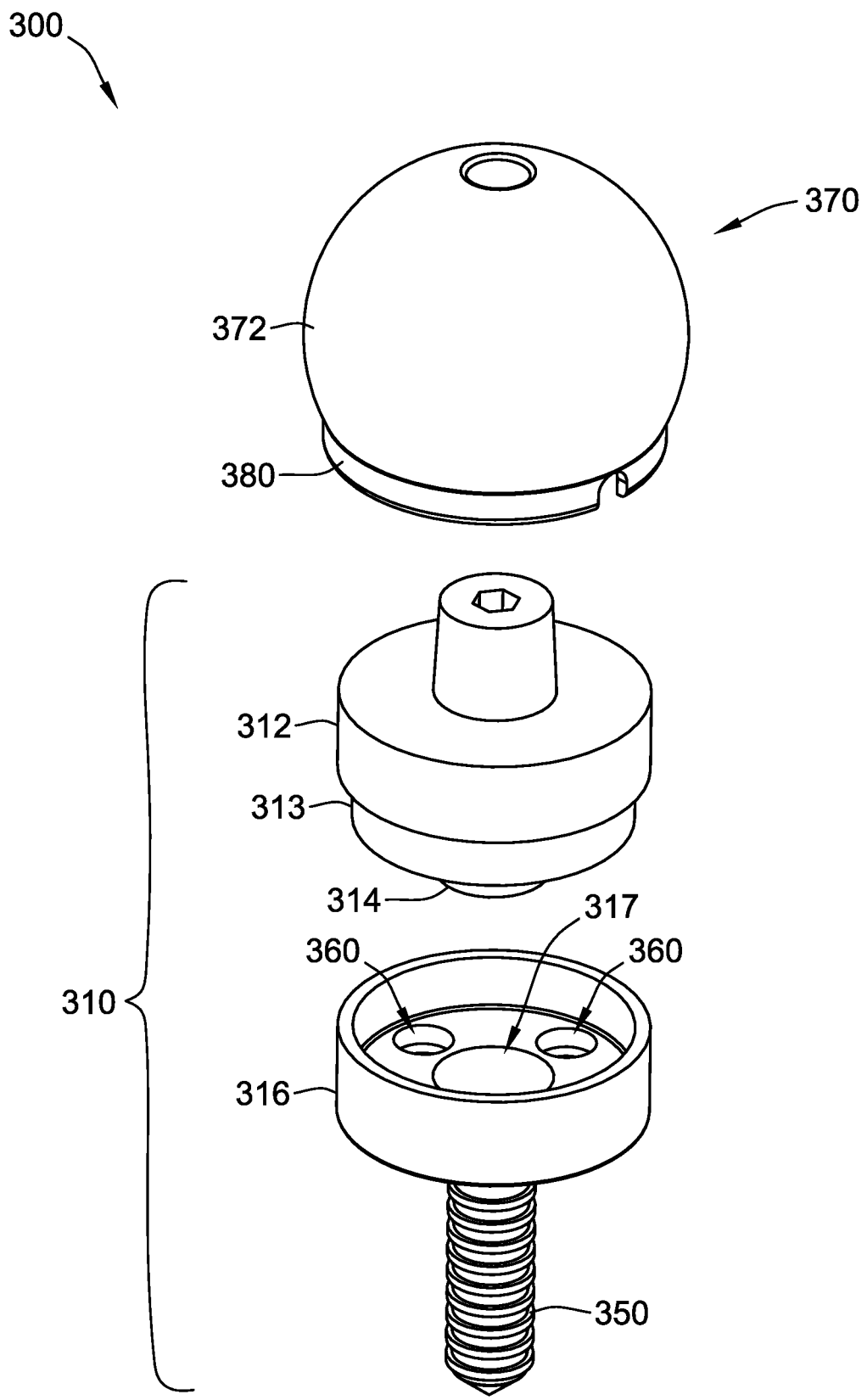
FIG. 9A illustrates a disassembled perspective view of a second alternative glenoid implant system, according to some implementations of the present disclosure.
Figure 9B:
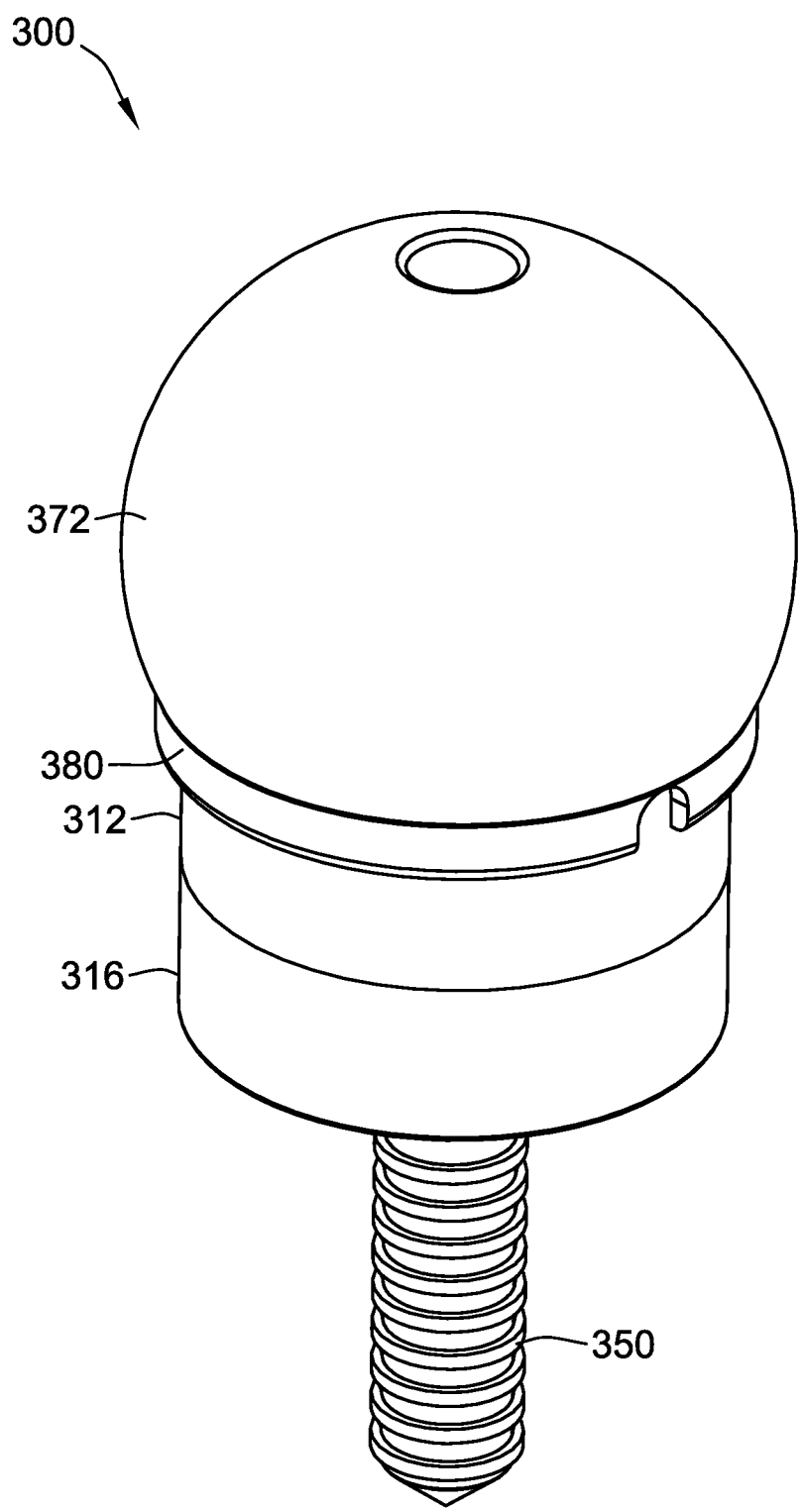
FIG. 9B illustrates an assembled perspective view of the second alternative glenoid implant system of FIG. 9A, according to some implementations of the present disclosure.

Thus, in some implementations, the present disclosure provides for a shoulder arthroplasty implant that allows easily accessible conversion from a TSA system to a RSA system. Referring to FIGS. 9A-9B, a second alternative glenoid implant system 300 is illustrated in its disassembled view of (FIG. 9A) and its assembled view (FIG. 9B), according to some implementations of the present disclosure. The glenoid implant system 300 includes an anchoring structure 310 that is the same as, or similar to, the anchoring structure 210 of the glenoid implant system 200 (FIG. 8), where like reference numbers are used for like elements, except that the anchoring structure 310 of the glenoid implant system 300 includes a baseplate 316 and a glenosphere adapter 312 (e.g., a reverse glenosphere adapter). The glenoid implant system 300 further includes a glenosphere 370 (e.g., a reverse glenosphere) configured to be coupled to the glenosphere adapter 312.

In some implementations, the glenoid implant system 300 (including, for example, the baseplate 316, the glenosphere adapter 312, and the glenosphere 370) can be used for RSA (e.g., a reverse procedure). For patients with large rotator cuff tears, shoulder arthritis, and/or shoulder arthropathy, reverse total shoulder replacement is a better option because the rotator cuff muscles no longer function. The reverse total shoulder replacement relies on the deltoid muscle, instead of the rotator cuff, to position and power the arm.

In some implementations, the baseplate 316 of the glenoid implant system 300 is the same as the baseplate 216 of the glenoid implant system 200. As such, when RSA is performed as a revision to TSA, the baseplate can stay in the patient, where the glenoid liner adapter 212 and the glenoid liner 270 can be replaced by the to the glenosphere adapter 312 and the glenosphere 370.

The glenosphere 370 is configured to be coupled to the glenosphere adapter 312. In turn, the glenosphere adapter 312 is configured to be coupled to the baseplate 316. The glenosphere adapter 312 includes stacked protuberances 313 and 314. The baseplate 316 includes a wall (e.g., a shell, a peripheral rim) configured to receive the first protuberance 313, similar to the coupling mechanism between the wall 215 and the first protuberance 213 of the glenoid implant system 200 (FIGS. 8A-8B). Additionally, or alternatively, in some implementations, the baseplate 316 includes a cavity 317 configured to receive the second protuberance 314, similar to the coupling mechanism between the cavity 217 and the second protuberance 214 of the glenoid implant system 200 (FIGS. 8A-8B). Additionally, or alternatively, in some implementations, the glenosphere adapter 312 is configured to be coupled to the baseplate 316 via a center screw.

In some implementations, the glenoid implant system of the present disclosure allows easily accessible conversion from a TSA system to a RSA system. For example, a glenoid implant assembly can include the following components: a baseplate (e.g., the baseplate 216 or the baseplate 316), a glenoid liner adapter (e.g., the glenoid liner adapter 212), a glenoid liner (e.g., the glenoid liner 170 or the glenoid liner 270), a glenosphere adapter (e.g., the glenosphere adapter 312), and a glenosphere (e.g., the glenosphere 370). Because RSA switches the locations between the head and the cup, RSA can be performed as a revision to TSA. As such, using the example glenoid implant assembly, the baseplate can remain in place during the revision to TSA, while the glenoid liner adapter and the glenoid liner can be replaced by the glenosphere adapter and the glenosphere.

One or more elements or aspects or steps, or any portion(s) thereof, from one or more of any of claims 1-25 below can be combined with one or more elements or aspects or steps, or any portion(s) thereof, from one or more of any of the other claims 1-25 or combinations thereof, to form one or more additional implementations and/or claims of the present disclosure.

While various examples of the present disclosure have been described above, it should be understood that they have been presented by way of example only, and not limitation. Numerous changes to the disclosed examples can be made in accordance with the disclosure herein without departing from the spirit or scope of the disclosure. Thus, the breadth and scope of the present disclosure should not be limited by any of the above described examples. Rather, the scope of the disclosure should be defined in accordance with the following claims and their equivalents.

What is claimed is:

1. A glenoid implant system comprising:
an anchoring structure having a base, a wall, and a ledge, the wall extending from a first surface of the base, the ledge extending generally along at least a portion of a first side of the wall thereby forming an undercut, the wall having a slot formed in a second opposing side of the wall; and
a glenoid liner configured to be removably coupled to the anchoring structure, the glenoid liner having a cap portion, a main body, and a deflectable finger, the cap portion having a first surface and a second opposing surface, the main body extending from the second opposing surface of the cap portion and including a lip configured to engage the undercut of the anchoring structure, the deflectable finger extending from the second opposing surface of the cap portion, the deflectable finger having a protrusion configured to engage the slot of the anchoring structure to aid in securing the glenoid liner to the anchoring structure,
wherein the ledge of the anchoring structure includes a first protrusion configured to engage a first corresponding notch formed in the main body of the glenoid liner, and wherein the anchoring structure further includes a second protrusion configured to engage a second corresponding notch formed in the lip of the main body of the glenoid liner.

2. The glenoid implant system of claim 1, wherein the base of the anchoring structure is generally circular, generally oval, generally bean shaped, generally egg shaped, generally tear-drop shaped, generally football shaped, or any combination thereof.

3. The glenoid implant system of claim 1, wherein the ledge of the anchoring structure extends from an inside surface of the wall as opposed to an outside surface of the wall.

4. The glenoid implant system of claim 1, wherein the anchoring structure is configured to be anchored in a glenoid cavity of a patient.

5. The glenoid implant system of claim 1, wherein the anchoring structure includes a baseplate and an adapter, and wherein the adapter is a glenoid liner adapter.

6. The glenoid implant system of claim 5, further comprising a glenosphere configured to be coupled to a glenosphere adapter.

7. The glenoid implant system of claim 1, wherein the wall extends about an entire perimeter of the base, and wherein the main body of the glenoid liner is configured to be encapsulated within the wall of the anchoring structure.

8. The glenoid implant system of claim 1, wherein the wall of the anchoring structure extends generally perpendicularly from the first surface of the base.

9. The glenoid implant system of claim 1, wherein the anchoring structure further includes a first anchoring peg extending from a second opposing surface of the base opposite the first surface of the base, and wherein the anchoring structure further includes a second anchoring peg extending from the second opposing surface of the base, and wherein the second anchoring peg is spaced from the first anchoring peg.

10. The glenoid implant system of claim 1, wherein the base of the anchoring structure further includes a plurality of through-holes for receiving one or more respective fasteners therethrough to aid in securing the anchoring structure to a glenoid fossa of a patient.

11. The glenoid implant system of claim 10, wherein a second opposing surface of the base is generally planar for coupling to a corresponding generally planar surface of the glenoid fossa of the patient.

12. The glenoid implant system of claim 10, wherein a second opposing surface of the base is generally convex for coupling to a corresponding generally concave surface of the glenoid fossa of the patient.

13. The glenoid implant system of claim 1, wherein the first corresponding notch is positioned generally between the cap portion of the glenoid liner and the lip of the main body of the glenoid liner.

14. The glenoid implant system of claim 1, wherein the second protrusion is positioned generally between the first protrusion of the ledge and the base of the anchoring structure.

15. The glenoid implant system of claim 1, wherein the first protrusion extends a first distance from the wall and the second protrusion extends a second distance from the wall, the second distance being less than the first distance.

16. The glenoid implant system of claim 1, wherein the first protrusion is stacked on the second protrusion in a stepped fashion.

17. The glenoid implant system of claim 1, wherein the glenoid liner is one monolithic part.

18. The glenoid implant system of claim 1, wherein the first surface of the cap portion of the glenoid liner is generally concave.

19. The glenoid implant system of claim 1, wherein the protrusion of the deflectable finger includes an elongated rib.

* * * * *